United States Patent [19]

Valorose, Jr. et al.

[11] Patent Number: 4,837,030

[45] Date of Patent: Jun. 6, 1989

[54] NOVEL CONTROLLED RELEASE FORMULATIONS OF TETRACYCLINE COMPOUNDS

[75] Inventors: Joseph J. Valorose, Jr., Montgomery; Raymond J. Biehl, Monsey; Nitin V. Sheth, Middletown; Walter A. Strathy, Pearl River; Michael K. Doelling, New City, all of N.Y.

[73] Assignee: American Cyanamid Company, Stamford, Conn.

[21] Appl. No.: 104,917

[22] Filed: Oct. 6, 1987

[51] Int. Cl.[4] .................. A61K 9/64; A61K 9/22; A61K 9/16; A61K 9/50

[52] U.S. Cl. .................... 424/456; 424/468; 424/469; 424/489; 424/490; 424/494; 424/497; 424/499; 424/500; 424/501

[58] Field of Search ............... 424/489, 490, 491, 494, 424/495, 456, 468, 469, 497, 499, 520, 501

[56] References Cited

U.S. PATENT DOCUMENTS

| | | | |
|---|---|---|---|
| 3,901,942 | 8/1975 | Bernardi et al. | 260/351.3 |
| 3,960,757 | 6/1976 | Morishita et al. | 427/213.36 |
| 4,038,315 | 7/1977 | Tobkes | 260/351.2 |
| 4,154,827 | 5/1979 | Cox et al. | 514/152 |
| 4,207,258 | 6/1980 | Broggi et al. | 260/351.5 |
| 4,500,458 | 2/1985 | Villax et al. | 260/351.5 |
| 4,622,244 | 11/1986 | Lapka et al. | 427/213.32 |

Primary Examiner—Thurman K. Page
Attorney, Agent, or Firm—Hedman, Gibson, Costigan & Hoare

[57] ABSTRACT

Pharmaceutical compositions comprising spherical granules including thereon or therein a 7- or 9-akylamino-6-deoxy-6-demethyltetracycline or an acid-addition salt thereof blended with at least one excipient are adapted to control the rate of drug release in the stomach and in the intenstine in order not to produce nausea or dizziness upon oral administration during antibacterial therapy.

42 Claims, 6 Drawing Sheets

NOVEL CONTROLLED RELEASE FORMULATIONS OF TETRACYCLINE COMPOUNDS

FIELD OF THE INVENTION

This invention is concerned with a pharmaceutical dosage form for the controlled release of antibacterial agents comprising tetracycline compounds. More specifically, it is concerned with spheres comprising a tetracycline compound blended with an excipient, the spheres being adapted to control the rate of release of the tetracycline in the human stomach and human intesting upon oral administration. When the spheres are filled into capsules or compressed into tablets, and the like, there are provided controlled release dosage forms of tetracycline compounds which do not produce the nausea or dizziness normally associated with other dosage forms.

BACKGROUND OF THE INVENTION

Tetracycline compounds are widely used in therapy primarily for their antimicrobial effect. A preferred family of such agents comprises the 7- or 9-alkylamino-6-deoxy-6-demethyltetracyclines, including the non-toxic acid-addition salts thereof. Commonly assigned Boothe et al, U.S. Pat. No. 3,148,212, and Petisi et al, U.S. Pat. No. 3,226,436, describe the preparation of this family of tetracycline compounds. Although they have achieved widespread use in oral dosage forms, particularly 7-dimethylamino-6-deoxy-6-demethyltetracycline hydrochloride, also known as minocycline hydrochloride, they have one drawback, and that is a tendency to cause CNS and gastrointestinal side effects including lightheadedness, dizziness, vertigo, nausea, vomiting and diarrhea. People on oral therapy with these drugs must, as a result, be cautioned about driving vehicles or using hazardous machinery, and also lowered patient compliance in continuing to take the drug naturally occurs.

In Bechgaard, U.S. Pat. No. 4,606,909, the placement of a sparingly soluble active substance, such as tetracycline, in an oral controlled relese dosage form is disclosed. The spraingly soluble active substance must be used with a dispersion-enhancing substance, such as an anionic detergent to promote solubility in intestinal fluids. The composition is formed into small spheres and enteric coated to eliminate any release of drug in the stomach. The coated spheres are tabletted or loaded into capsules. There is no teaching that such a dosage form can be used to avoid dizziness and/or nausea associated with tetracycline therapy. Moveover the requirement to use a dispersion-enhancing substance, especially an anionic detergent, is a negative factor.

McAinsh et al, U.S. Pat. No. 4,138,475, disclose that propranolol or a pharmaceutically-acceptable salt thereof can be formulated into a sustained release pharmaceutical composition by mixing with a non-water-swellable microcrystalline cellulose and forming into spheroids. These spheres are coated with a heavy film of hydroxypropyl methylcellulose and/or a plasticizer to eliminate any release of the drug in the stomach. The film coated spheroids are then filled into gelatin capsules. Apart from the fact that propranolol is used as a beta-blocker to treat heart problems and not for oral antimicrobial use, the dosage form of the McAinsh patent is primarily adapted, like all sustained release dosage forms, to reduce the total number of capsules needed for a daily dose. Propranol is often taken 3 to 4 times daily, whereas most recent oral tetracyclines are given once or twice a day. Furthermore, there is no hint or suggestion in McAinsh et al that the pharmaceutical compositions should be used with tetracycline compounds. Finally, there is no mentioned whatsoever that such dosage forms can be used with propranolol, or for that matter, with any other drug, to overcome adverse reactions, especially CNS and gastrointestinal side effects.

Parke-Davis has recently offered for use by the medical profession capsules under the trademark DORYX® containing specially coated pellets of doxycycline hyclate for oral administration. See, Physicians Desk Reference, 1987, Medical Economics Company, Oradell, NJ, pages 1487-1489. In contrast to minocycline hydrochloride, and its isomers and analogs, doxycycline hyclate does not contain an alkyl amino group at either the 7- or the 9-position. The Parke-Davis pellets are said to comprise in addition to the doxycycline compound, lactose, microcrystalline cellulose and povidone (polyvinylpyrrolidone). The film coating is both thick, e.g., 15-20% by weight based on the granules, and necessary. The disclosure in the Physicians Desk Reference is unclear as to the advantages for using such film coated pellets but it is believed that the film is used to minimize release in the stomach and any resulting gastric distress.

To overcome the problems of both CNS and gastric side effects mentioned above, a need still exists for an improved controlled release tetracycline containing composition, especially one without film coatings, particularly, thick film coatings and this has been met by the present invention in a way not suggested by the foregoing prior art. Although spherical granules will be used, they will be specially formulated to control release on oral administration. Preferably, they will release a minor portion of the tetracycline compound slowly in the human stomach and then rapidly release the remainder in the human intestine. This is accomplished by preparing microspheres containing thereon or therein the drug blended with one or more judiciously selected excipients and adapting the spheres to accomplish the controlled release, while omitting any film coating whatsoever or using only an ultra thin layer of polymer film which erodes only slowly in the stomach but very rapidly in the small intesting. While reasons for the attained advantages in reducing side effects are not clearly understood at this time, it is believed that slow release of the tetracycline compound in the stomach avoids gastric upset and rapid release of the remainder of the tetracycline compound in the small intestine can be better tolerated in terms of CNS side effects because there is no extreme elevation in short-term blood levels. Although the full scope of the advantages of this invention is believed to be broadly applicable for tetracycline compounds in general, it appears to be uniquely suitable for use with 7- or 9-alkylamino-6-deoxy-6-demethyltetracycline compounds.

SUMMARY OF THE INVENTION

According to the present invention there are provided spheronized pharmaceutical compositions comprising granules which include or or in said granules an effective antibacterial amount of a 7- or 9-alkylamino-6-deoxy-6-demethyltetracycline or a non-toxic acid addition salt thereof blended with an effective amount of at least one pharmaceutically acceptable excipient, the granules being adapted to control the rate of release of the tetracycline in the human stomach and human intestine upon oral administration. In a preferred embodiment, controlling the rate of release comprises release comprises retarding the rate of release of said tetracycline compound in the human stomach and promoting rapid release of said tetracycline compound in the human intesting upon oral administration.

The present invention also contemplates controlled release pharmaceutical compositions in oral dosage unit form comprising A. A gelatin capsule filled solely with
B. beads having an average diameter of from about 0.1 to about 2.5 millimeters, each bead being similar in composition and comprising spherical granules which include on or in said granules an effective antibacterial amount of a 7- or 9-alkylamino-6-deoxy-6-demethyltetracycline or a non-toxic acid adition salt thereof blended with an effective amount of at least one pharmaceutically acceptable excipient, the granules being adapted for control the rate of release of the tetraacycline compound in the human stomach an in the human intestine upon oral administration.

It is also among the features of the invention to provide oral dosage units by forming the beads into tablets.

In some features of the invention, especially when the drug is coated on spherical seeds, the spheres will include an ultra-thin layer of a polymer substantially uniformly coating each of said spheres, the polymer being slowly erodable in the human stomach and rapidly erodable in the human small intestine upon oral administration.

In both instances, a water-soluble tetracycline compound, i.e., one which requires less than 500 parts by volume of water to dissolve 1 part by weight of the tetracycline compound at ambient temperature is preferred. Moreover, in both instances, using either uncoated spheres or film-coated spheres, the tetracycline compound will be more than 60 percent released, and preferably substantially completely released, i.e., more than 90 percent released, from the spherical granules in not less than about 20 minutes nor more than about 90 minutes when suspended in deionized water (pH about 6) at body temperatures e.g., 37° C., at a drug concentration of about 100 mg/900 ml w/v. In the film coated version, ultra thin coatings are preferred for this reason. Ultrathin means, for purposes of this disclosure, that the weight of the film will be from 2 to less than about 10, preferably from about 2 to about 5 percent by weight based on the weight of the film coated granules.

DETAILED DESCRIPTION OF THE INVENTION

Although broadly applicable to tetracycline compounds in general, it is preferred for purposes of this invention to use members of the tetracycline family comprising substituted 7- and/or 9-amino tetracyclines which may be represented by the following general formula:

where R is hydrogen or methyl and $R_1$ and $R_2$ are hydrogen, mono(lower alkyl)amino or di(lower alkyl)amino with the proviso that $R_1$ and $R_2$ cannot both be hydrogen. Typical compounds represented by the above general formula are, for example, 7-methylamino-6-deoxy-6-demethyltetracycline, 7-ethylamino-6-deoxy-6-demethyltetracycline, 7-isopropylamino-6-deoxy-6-demethyltetracycline, 9-methylamino-6-deoxy-6-demethyltetracycline, 9-ethylamino-6-deoxy-6-demethyltetracycline, 9-isopropylamino-6-deoxy-6-demethyltetracycline, 7,9-di(ethylamino)-6-deoxy-6-demethyltetracycline, 7-dimethylamino-6-deoxy-6-demethyltetracycline, 9-dimethylamino-6-deoxy-6-demethyltetracycline, 7-methylamino-6-deoxytetracyline, 9-ethylamino-6-deoxytetracyline, 7,9-di(methylamino-6-deoxytetracycline, 7-diethylamino-6-deoxytetracycline, 9-diethylamino-6-deoxytetracycline, 7,9-di(methylethylamino)-6-deoxytetracycline, 7-methylamino-9-ethylamino-6-deoxytetracycline, and 9-methylamino-5-hydroxy-6-deoxytetracycline.

Preferred members of this family comprise tetracycline compounds selected from
(a) 7-dimethylamino-6-deoxy-6-demethyltetracycline;
(b) 7-methylamino-6-deoxy-6-dimethyltetracycline;
(c) 9-methylamino-6-deoxy-6-demethyltetracycline;
(d) 7-ethylamino-6-deoxy-6-demethyl-tetracycline;
(e) 7-isopropylamino-6-deoxy-6-demethyltetracycline;
(f) a non-toxic acid addition salt of (a)–(e), inclusive or
(g) a mixture of any of the foregoing.

Special mention is made of the tetracycline compound 7-dimethylamino-6-deoxy-6-demethyltetracycline and its non-toxic acid addition salts, e.g., hydrochloric, sulfonic, trichloroacetic acid salts, and the like, especially preferably the hydrochloric acid addition salts. The last named compound is also known as minocycline hydrochloride. These compounds and methods for their preparation are disclosed in the above-mentioned U.S. Pat. Nos. 3,148,212 and 3,226,436.

For best results, the controlled release composition of this invention in dosage unit form may, for example, contain from 25 to 200 mg, and more preferably 50 and 100 mg, of the tetracycline compound, for example, minocycline hydrochloride.

In order to provide one of the pharmaceutical dosage forms which is subject of this invention, namely, that in which the drug is in, rather then on, the spheres, the tetracycline compound, e.g., minocycline hydrochloride, in the form of a powder, is blended with the desired amount of the pharmaceutical excipient at low speed. Water is then added slowly, with continuous mixing, until a granulation of the desired consistency is obtained.

The wet granulation is then extruded using suitably sized pierced plates and spheronized at high speeds. The wet spheres are then dried in a fluidized system to a suitable moisture level, e.g., about 3 to 5 percent by weight. The fluid bed system provides rapid drying of the spheres, giving then a smooth surface with homogeneous drug distribution.

If spheres having the drug as a surface layer are to be prepared, the well-known technique of coating seeds, e.g., nonpareil seeds is used. Such seeds are generally of about 0.1 mm in size and comprise for example, a blend of sugar and starch. The drug is mixed with the excipient, e.g., microcrystalline cellulose, and a binder, e.g., gelatin, and coated on the seeds using a rotogranulator, a fluid bed apparatus or similar pharmaceutical dosage form equipment. This technique will also be exemplified hereinafter.

The term "spheres" is well known in the pharmaceutical art, and means spherical granules having a diameter of approximately 0.1 to 2.5 millimeters, preferably from 0.5 to 2, and most preferably from 0.8 to 1.2 millimeters.

Although many pharmaceutical excipients are known, many but not all of them will be suitable for use in this invention. Judicious selection will be easy however with the above-mentioned requirements and the test procedures herein being kept in mind. There should be used an excipient with a known degree of solubility and swellability in the respective liquid juices of the stomach and the small intestine. Those skilled in this art will be familiar with pharmaceutical excipients and most of them are listed in standard references, for example, Remington's Pharmaceutical Sciences, 1980, 16th Edition, Philadelphia College of Pharmacy and Science, Chapter 67, Pharmaceutical Necessities, pages 1225–1267. Although a single excipient can be used, e.g., microcrystalline cellulose, as will be shown in the examples, desirable results will require more care in selecting an appropriate amount of tetracycline compound to be used in the sphere. For example, with a single excipient, e.g., microcrystalline cellulose, minocycline hydrochloride should comprise 60 to 70 percent by weight of the total weight of the sphere, although the drug loading can be changed, if desired. With more than one excipient, less tetracycline compound can generally be used. Because of these factors, somewhat wider latitude in formulation will be possible following the use of combinations of excipients. Illustrative, but by no means exhaustive, of the exipients suitable for use herein are microcrystalline cellulose, polyvinylpyrrolidone, hydroxypropylmethyl cellulose, microcrystalline cellulose and lactose, microcrystalline cellulose and sodium carboxymethylcellulose, mixtures of any of the foregoing, and the like.

Suitable forms of microcrystalline cellulose are, for example, the materials sold as Avicel-PH-101 and Avicel-PH-105 (available from FMC Corporation, American Viscose Division, Avicel Sales, Marcus Hook, PA., U.S.A.). A suitable mixture of microcrystalline cellulose and sodium carboxymethyl cellulose is, for example, the material sold as Avicel RC-581 by FMC Corporation. Generally, it has been found that the uncoated spheres may, for example, contain 10 to 70 percent by weight of minocycline hydrochloride or other tetracycline compound and 90 to 30 percent by weight of excipient or excipients, as the case may be, respectively, although, as mentioned, the drug loadings can vary.

The spherical granules of this invention can be made using conventional pharmaceutical production equipment. To make granules containing the drug, it is convenient, for example, to blend powdered tetracycline compound and powdered excipient in a dough mixer, e.g., a Hobart mixer, and then to granulate with a liquid medium, e.g., water, until the proper consistency for extrusion is realized. The granulated mass is then extruded at high speed though a suitably sized, e.g., 0.8 or 1.0 mm., perforated plate and spheronized at high speed. The wet spheres are then conveniently dried in conventional equipment such as tray driers. Preferably they are dried, e.g., in a conventional fluidizing system to a low moisture level, e.g., about 3 to about 5 percent. Alternatively, other techniques can be used, such as rotogranulation techniques (Glatt) or any other techniques used to make spheres or pellets of this general type, such as Freund CF Granulation, or any other technique.

If the drug is to be coated on seeds, typically, 30–35 mesh nonpareil seeds will be coated with a water dispersion of tetracycline compound, microcrystalline cellulose and gelatin in a Glatt Rotogranulator. The resultant particle size will be between about 850 and 425 micron.

The film forming polymer, if used, can vary widely in type, and amount, which correlates to film thickness. It is important, however, that any film forming polymer either be somewhat erodable in gastric juice and/or used in ultrathin layer or layers to permit release of a minor proportion of the tetracycline compound in the stomach, the importance of which has been set forth above. Although from 2 to less than about 10 weight percent of film content based on the weight of the film coated spheres is suitable for most readily gastric juice erodable polymers, it is preferred to use 2 to 5 percent of any film because thin layers of all polymers, even those of somewhat higher resistances to acidic gastric juices, will permit release of the required small amounts of tetracycline compound in the stomach.

Illustrative but not limiting film forming polymers are cellulose and acrylic acid based polymers. Particularly to be mentioned are methyl cellulose, ethyl cellulose, hydroxyethyl cellulose, hydroxypropyl cellulose, hydroxypropyl methyl cellulose, hydroxypropyl methyl cellulose phthalate, cellulose acetate phthalate, hydroxypropyl methylcellulose succinate, polymers and copolymers of (meth)acrylic acid and (meth)acrylic acid methyl ester and mixtures of any of the foregoing. The coatings can include conventional additives, such as plasticizers, pigments, colorants, etc. The plasticizers can include mineral oil, high boiling esters, vegetable oils and the like. Commercial coating compositions found to be useful include Eudragit ® a product of Rohm Pharma, Weiterstadt, Germany and Surelease ®, a product of Colorcon, Inc., West Point, PA. The former comprises an anionic polymerizate of methacrylic acid and methyl methacrylate. The latter comprises an aqueous dispersion of ethyl cellulose, dibutyl sebacate, oleic acid, fumed silica, and ammonium hydroxide.

Preferred as coating materials are ethyl-cellulose and hydroxypropyl methylcellulose, and the commerical coatings exemplified herein.

A suitable form of ethylcellulose is one having a viscosity in the range of 5 to 100 cps at 20° C. (U.S. National Formulary XIII) (content of ethoxy groups 44 to 51% by weight), and more particularly a viscosity of 50 cps at 20° C. (content of ethoxy groups 48 to 49% by weight). A suitable form of hydroxypropyl methylcellulose is one having a viscosity in the range 3 to 100 cps at 20° C. (U.S. National Formulary XII), and more particularly a viscosity of 6 cps at 20° C.

The spheres containing tetracycline compound thereon or therein can, if desired, be coated with an aqueous or organic solvent solution of the desired film forming polymer, using fluid bed technology or pan-coating, and the like, but preferably fluid beds are used.

For best results, if a film coating is used, a 1 percent weight gain level precoat and overcoat of hydroxypropyl methylcellulose are preferred in addition to the standard coating when using aqueous formulations.

Several formulations comprising polymers suitable for use as film coatings in certain embodiments of this invention are shown in Tables I, II, III and IV.

TABLE I

COATING FORMULATIONS FOR MINOCYCLINE HYDROCHLORIDE SPHERES

| Ingredients | Formulation Number (% W/W) | | | | | |
| --- | --- | --- | --- | --- | --- | --- |
| | 1* | 2 | 3** | 4** | 5*** | 6* |
| Hydroxypropyl methylcellulose phthalate (HPMCP) | 75 | 67.5 | 60 | 56.25 | 52.5 | 37.5 |
| Hydroxypropyl methylcellulose (HPMC) | 0 | 7.5 | 15 | 18.75 | 22.5 | 37.5 |
| Mineral Oil | 15 | 15 | 15 | 15 | 15 | 15 |
| Opaspray K-1-2562**** | 10 | 10 | 10 | 10 | 10 | 10 |

*Formulations No. 1, 2 and 6 were applied at 4% weight gain level with organic solvents such as methylene chloride or methanol.
**Formulations No. 3 and 4 were applied at 2% and 4% weight gain level.
***Formulation No. 5 was applied at 4% and 8% weight gain level.
****Colorcon Inc., orange-colored dye composition.

TABLE II

PRECOAT/OVERCOAT FORMULATION FOR MINOCYCLINE HYDROCHLORIDE SPHERES

| INGREDIENT | % (W/W) |
| --- | --- |
| Hydroxypropyl methylcellulose | 71 |
| Sodium lauryl sulfate | 4 |
| Mineral Oil | 25 |
| Water (added at 9 times the total weight of the above solids) | |

This solution is applied at a 1% weight gain level, as a precoat and again as an overcoat on minocycline hydrochloride spheres when applying aqueous coatings.

TABLE III

COATING FORMULATION FOR MINOCYCLINE HYDROCHLORIDE SPHERES

| INGREDIENT | % (W/W) |
| --- | --- |
| Surelease ® | 60 |
| Water | 40 |

This solution is applied at 2, 3 and 5% weight gain levels to minocycline hydrochloride spheres.

TABLE IV

COATING FORMULATION FOR MINOCYCLINE HYDROCHLORIDE SPHERES

| INGREDIENT | % (W/W) |
| --- | --- |
| Surelease ® | 77 |
| Eudragit ® L30D* | 20 |
| Hydroxypropyl methylcellulose | 3 |
| Water (added at 6 times the total weight of the above solids) | |

*Product of Rohm Pharma, Weiterstadt, Germany

This solution is applied at 2 to 10% weight gain levels.

DESCRIPTION OF THE PREFERRED EMBODIMENTS

The invention will be more fully described by the following Examples.

EXAMPLE 1

A 300 g portion of minocycline hydrochloride powder was mixed uniformly with 300 g of microcrystalline cellulose in a Hobart mixer (model C-100) at low speed. The powder blend was then granulated with a total of 280 ml of water, by adding the water very slowly and mixing continuously until the proper consistency of granulation for extrusion was realized.

The granulated mass was extruded at high speed through a 0.8 mm plate in an NICA system (model S450) and spheronized at high speed. The wet spheres were dried for 40 minutes in an Uni-Glatt (model 82/E) at 70° C. air input, to a 4 percent moisture level. Fluid bed drying provided rapid drying of spheres, giving a uniform smooth surface and homogeneous drug distribution.

EXAMPLE 2

The procedure of Example 1 is repeated, using 40 parts by weight of minocycline hydrochloride to 60 parts by weight of microcrystalline cellulose. Uncoated spheres in accordance with this invention are obtained.

EXAMPLE 3

The procesure of Example 1 is repeated, replacing 40 percent by weight of the microcrystalline cellulose with lactose monohydrate. Uncoated spheres in accordance with this invention are obtained.

EXAMPLE 4

The procedure of Example 1 is repeated, replacing 40 percent by weight of the microcrystalline celulose with a mixture of microcrystalline cellulose and sodium carboxymethylcellulose (Avicel ® RC-581). Uncoated spheres in accordance with this invention are obtained.

EXAMPLE 5

Batches of minocycline hydrochloride spheres, prepared as described in Example 1, were subject to fluid bed coating, using the coating solutions and precoat and overcoat techniques described hereinabove.

EXAMPLE 6

Using 30–35 mesh nonpareil seeds, a suspension of 7-dimethylamino-6-deoxy-6-demethyltetracycline hydrochloride, microcrystalline cellulose, Avicel PH 105, gelatin, 125 bloom, and water was applied using a Glatt Rotogranulator. The solids to water ratio was 0.8125:1.000 and the final composition w/w of the pellets was: tetracycline compound, 43.3%, 30–35 mesh nonpareil seeds, 37.4%, microcrystalline cellulose, 14.3% and gelatin, 4.8%. The particle size of the drug coated spheres was between 850 and 425 microns. The foregoing pellets were provided with an ultrathin film coating by combining Eudragit ® L30D, titanium dioxide, talc, and polyvinylpyrrolidone in a water medium, by techniques described above.

If, in the film coating composition, the concentration of the water soluble component (polyvinylpyrrolidone) is varied inversely to that of the acid insoluble component (Eudragit ®) one is able to vary the rate of release of the tetracycline compound with precision in the stomach region.

Figure 1:
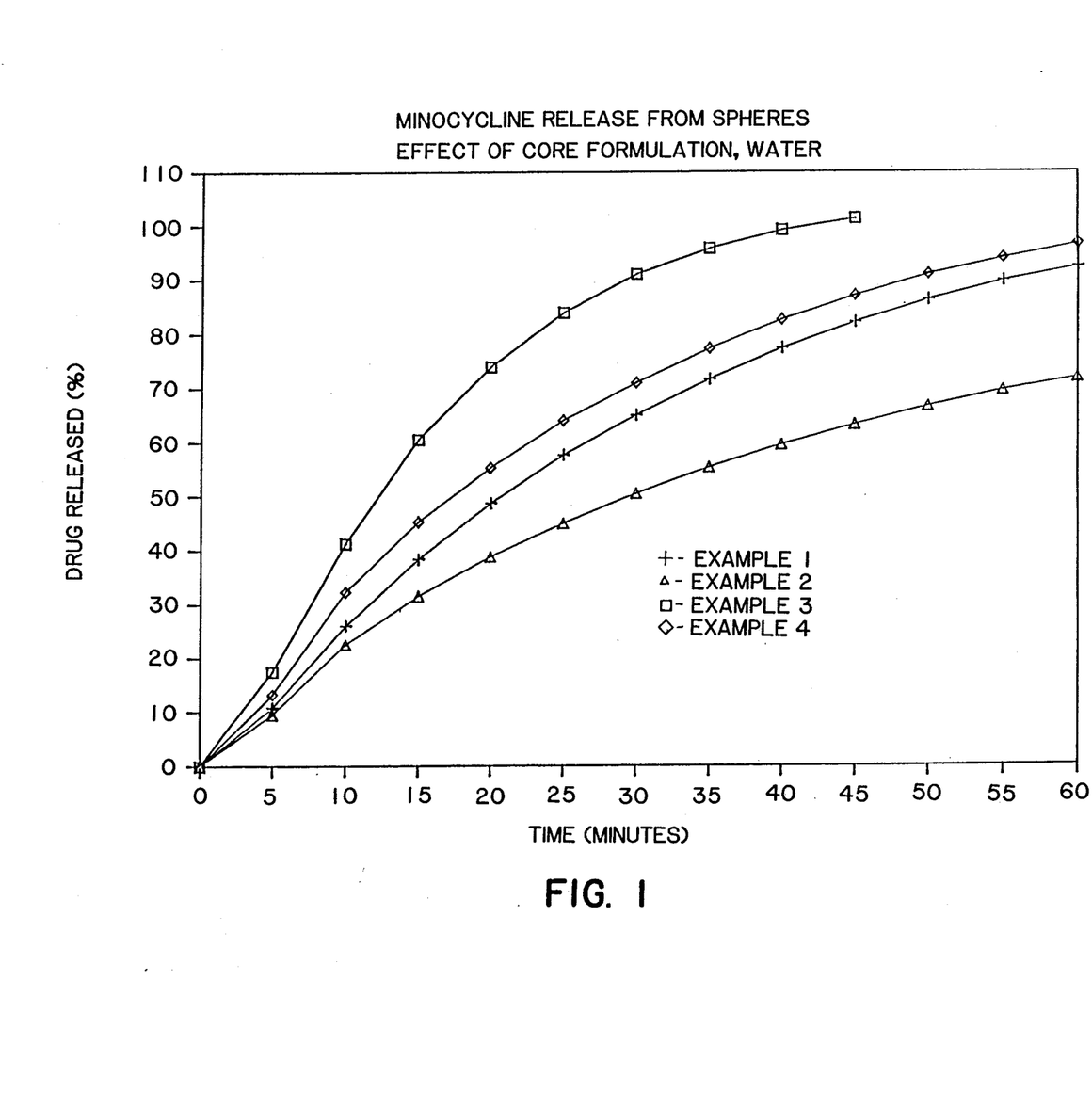
FIG. 1 is a graphical representation of the release of minocycline hydrochloride from uncoated spheres in accordance with this invention in deionized water, pH 6.
Figure 2:
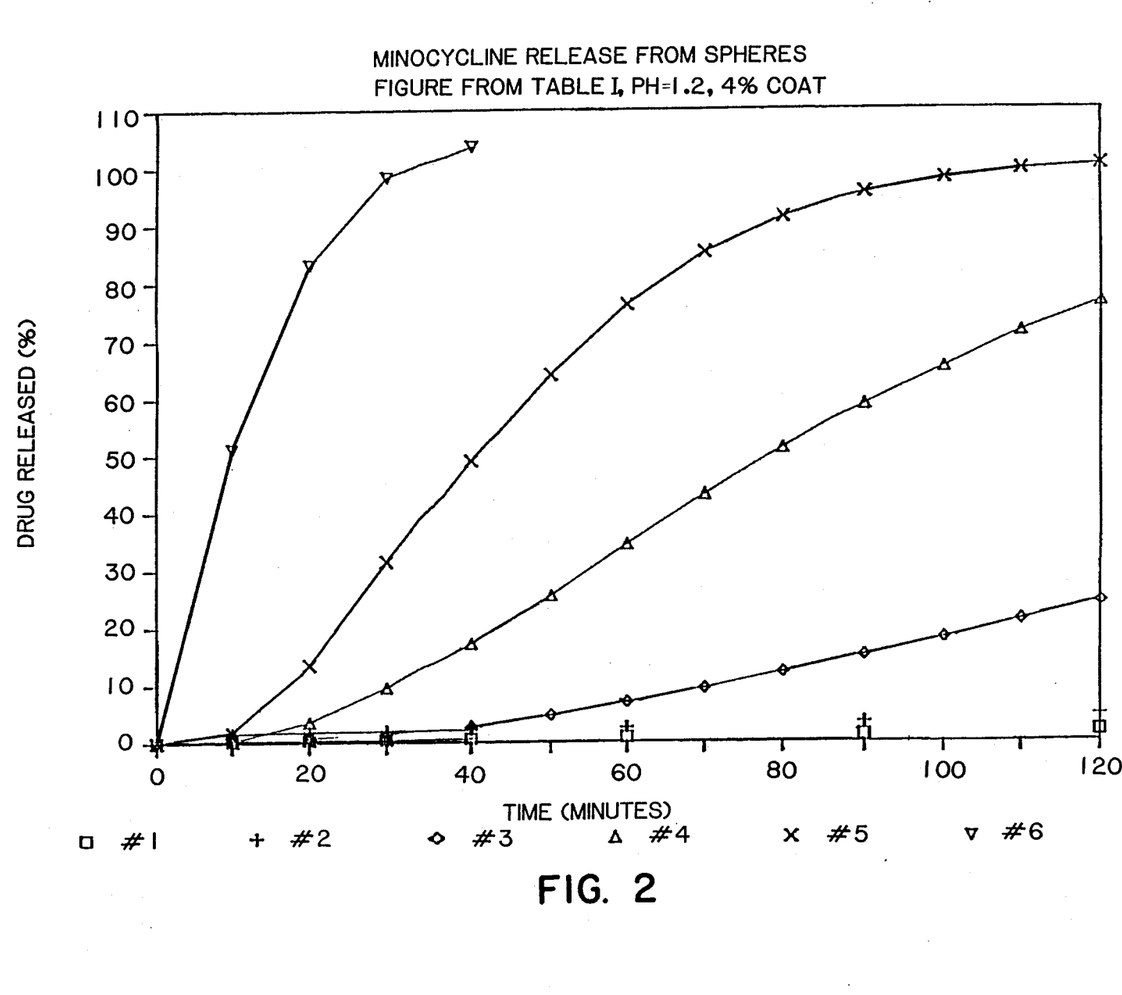
FIGS. 2, 4, and 5 are graphical representations of the release of minocycline hydrochloride from film coated spheres in accordance with this invention in synthetic gastric juice.
Figure 3:
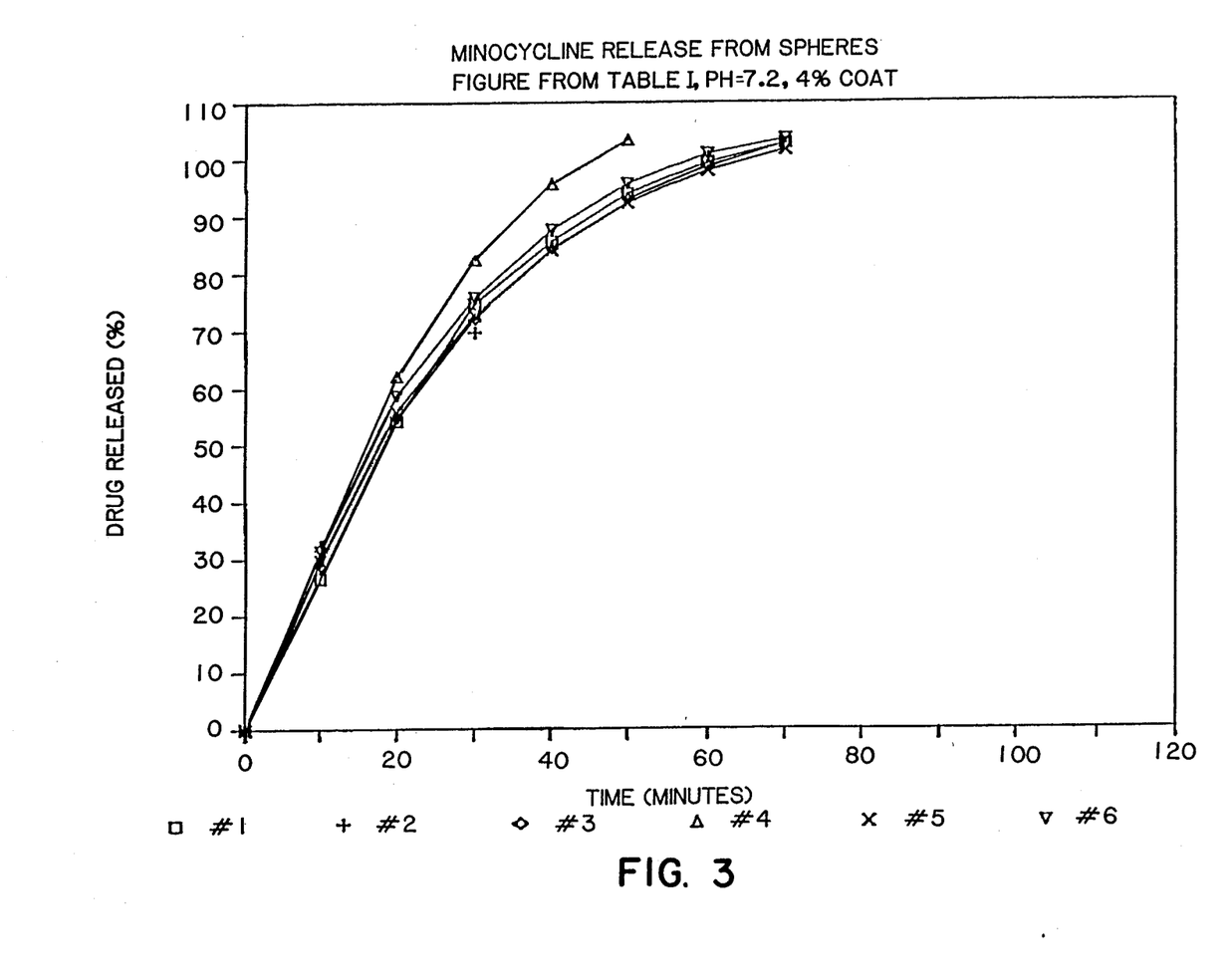
FIGS. 3 and 6 are graphical representations of the minocycline hydrochloride from film coated spheres in accordance with this invention in synthetic intestinal fluid.
Figure 4:
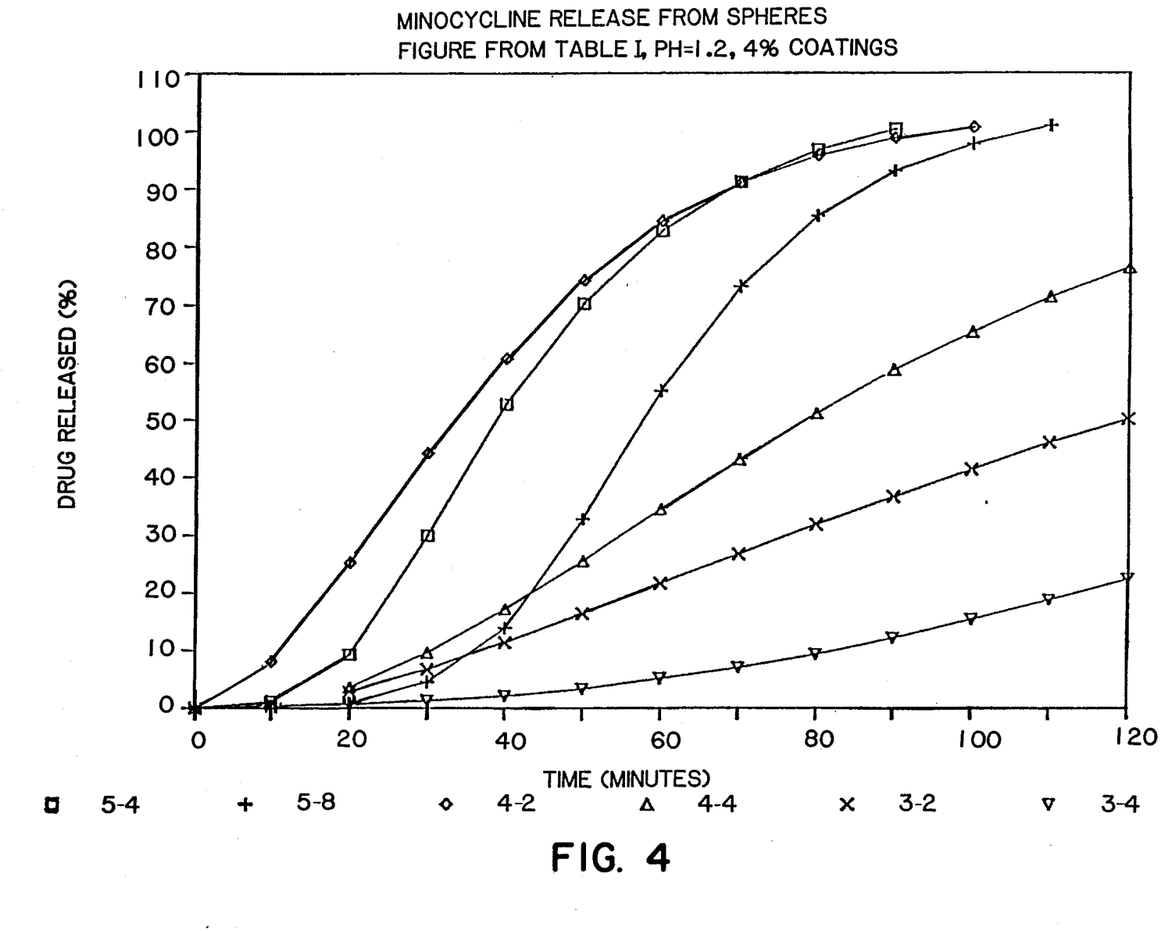
Figure 5:
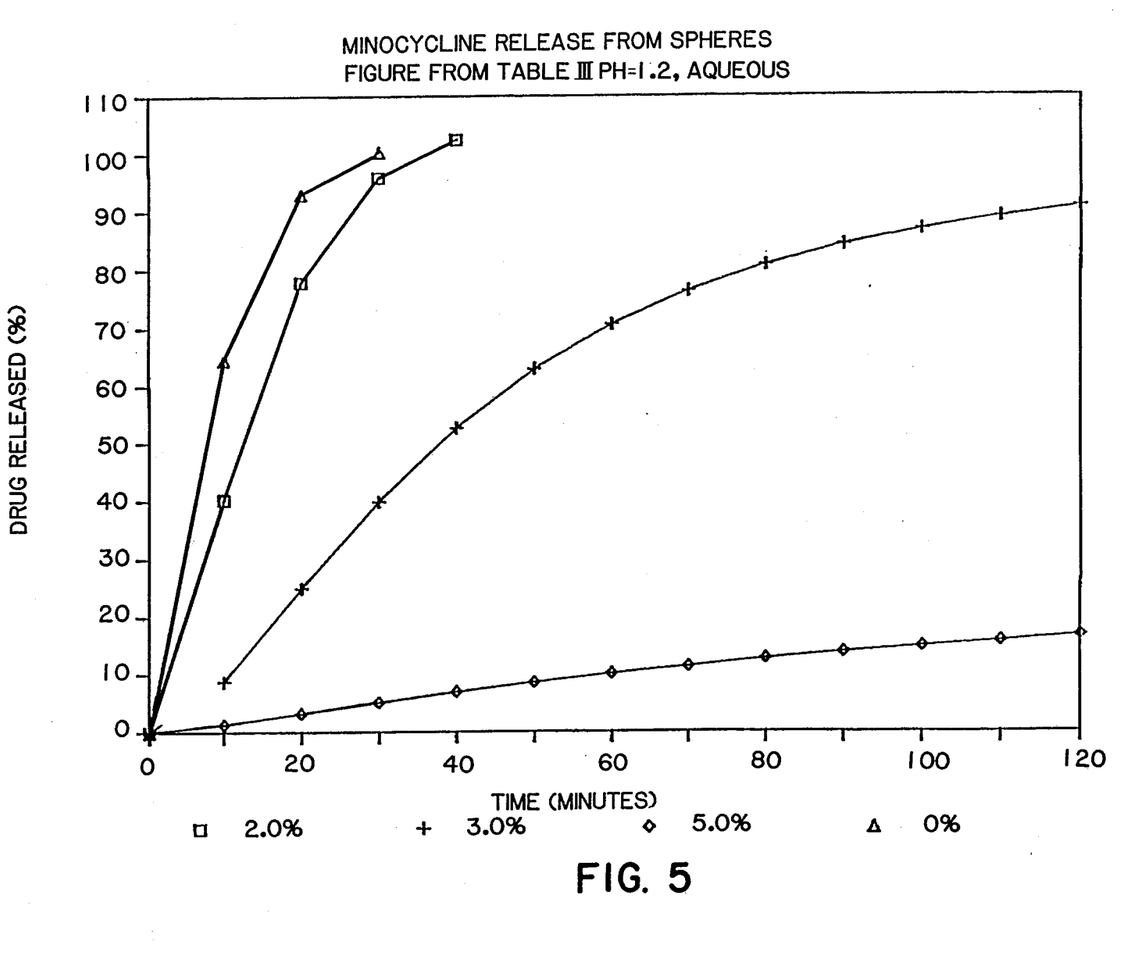
Figure 6:
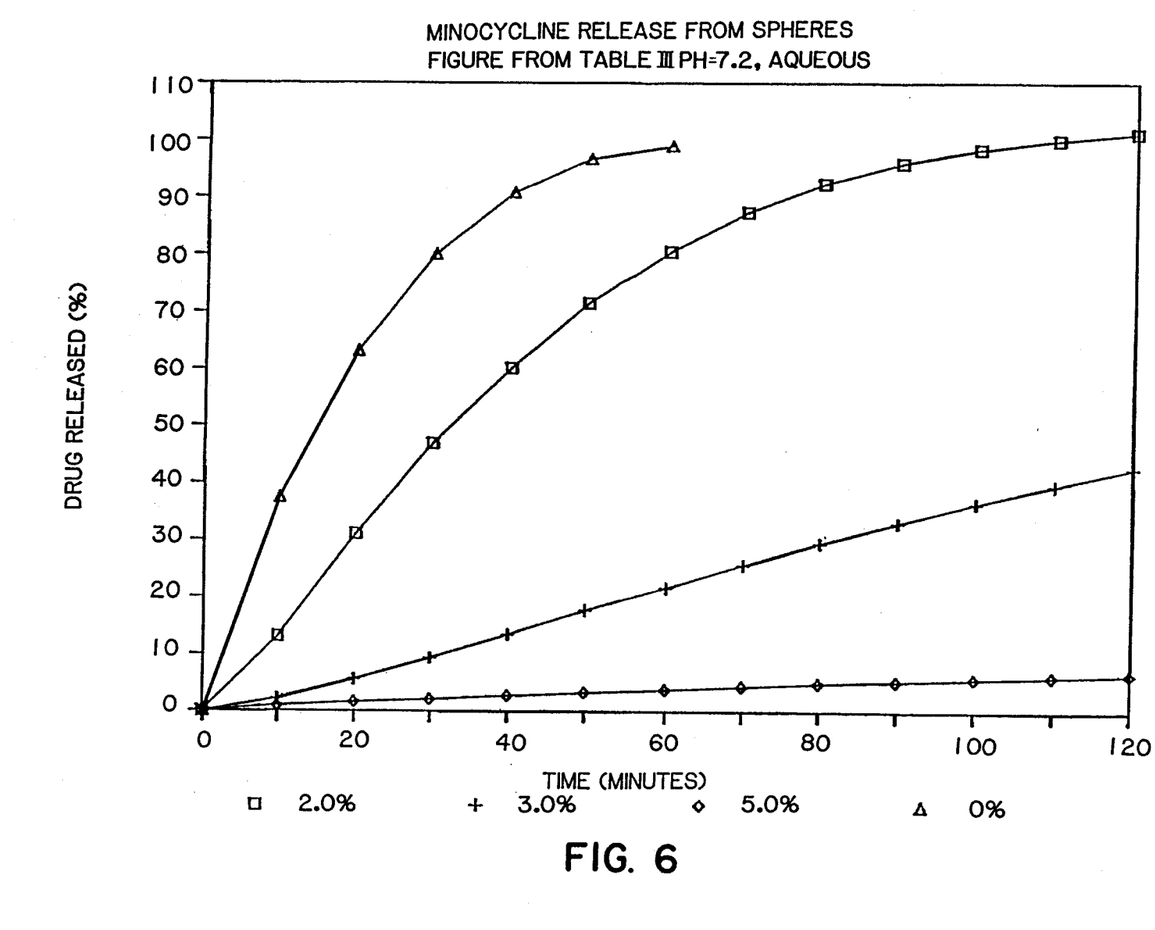

The results, in terms of control release, from some of these various formulations and techniques, were determined by U.S.P. XXI method in water and in simulated gastric and in intestinal pH conditions. The results appear in FIGS. 1-6 in graph form. The results are strongly indicative that the dosage units of this invention will deliver therapeutically active amounts of minocycline hydrochloride to the intestine, while liberating only small amounts of the tetracycline compound in the stomach, thereby avoiding undesirable side effects such as dizziness and nausea.

The above-mentioned patents and publications are incorporated herein by reference.

Many variations will suggest themselves to those skilled in this art in light of the foregoing detailed description. For example, instead of 7-dimethyl-6-deoxy-6-demethyltetracycline hydrochloride, the free base, the sulfuric acid and the trichloroacetic acid addition salts can be used. Instead of 7-dimethyl-6-deoxy-6-demethyltetracycline hydrochloride, the hydrochlorides of the following compounds can be used: 7-methylamino-6-deoxy-6-demethyltetracycline; 9-methylamino-6-deoxy-6-demethyltetracycline; 7-ethylamino-6-deoxy-6-demethyltetracycline; and 7-isopropylamino-6-deoxy-6-demethyltetracycline. As a film former, ethyl cellulose can be used alone. The pellets can be filled into either hard gelatin or soft gelatin capsules in conventional capsule-filling machines, to provide 50 and 100 milligrams of minocycline hydrochloride content in each capsule. The spheres can also be mixed with conventional pharmaceutical binders and/or excipients and compressed into tablets. All such obvious variations are within the full intended scope of the appended claims.

We claim:

1. A spheronized pharmaceutical composition spherical comprising granules which include on or in said granules an effective antibacterial amount of a 7- or 9-(lower)alkylamino-6-deoxy-6-demethyltetracycline or a non-toxic acid addition said thereof blended with an effective amount of at least one pharmaceutically acceptable excipient, said granules being adapted to control the rate of release of said 7- or 9-(lower)alkylamino-6-deoxy-6-demethyl tetracycline in the human stomach and human intesting upon oral administration.

2. A pharmaceutical composition as defined in claim 1 wherein controlling the rate comprises retarding the rate of release of said 7- or 9-(lower)alkyl-amino-6-deoxy-6-demethyl tetracycline compound in the human stomach and promoting rapid release of said tetracycline compound in the human intestine upon oral administration.

3. A pharmaceutical composition as defined in claim 1 wherein each of said spherical granules includes an ultrathin layer of a polymer substantially uniformly coating each of said spherical granules, said polymer being slowly erodable in the human stomach and rapidly erodable in the human small intestine upon oral administration.

4. A pharmaceutical composition as defined in claim 1 wherein said 7- or 9-(lower)alkylamino-6-deoxy-6-demethyl tetracycline compound is substantially completely released from said spherical granules in not less than about 20 minutes nor more than about 90 minutes when suspended in deionized water at ambient temperature at a drug concentration of about 100 mg of drug/900 ml of water.

5. A pharmaceutical composition as defined in claim 3 wherein said 7- or 9-(lower)alkylamino-6-deoxy-6-demethyl tetracycline compound is substantially completely released from said spherical granules in not less than about 20 minutes nor more than about 90 minutes when suspended in deionized water at ambient temperature at a drug concention of about 100 mg/900 ml of water.

6. A pharmaceutical composition as defined in claim 1 wherein said 7- or 9-(lower)alkylamino-6-deoxy-6-demethyl tetracycline is selected from
(a) 7-dimethylamino-6-deoxy-6-demethyl tetracyline;
(b) 7-methylamino-6-deoxy-6-demethyltetracycline;
(c) 9-methylamino-6-deoxy-6-demethyltetracycline;
(d) 7-ethylamino-6-deoxy-6-demethyltetracycline;
(e) 7-iospropylamino-6-deoxy-6-demethyltetracyline;
(f) a non-toxic acid addition salt of (a)–(e) inclusive; or
(g) a mixture of any of (a)–(f).

7. A pharmaceutical composition as defined in claim 6 wherein said 7- or 9-(lower)alkylamino-6-deoxy-6-demethyl tetracycline compound is selected from 7-dimethylamino-6-deoxy-6-demethyltetracycline or an acid addition salt thereof.

8. A pharmaceutical composition as defined in claim 7 wherein said 7- or 9-(lower)alkylamino-6-deoxy-6-demethyl tetracycline compound comprises 7-dimethylamino-6-deoxy-6-demethyltetracycline hydrochloride.

9. A pharmaceutical composition as defined in claim 1 wherein said pharmaceutical excipient comprises microcrystalline cellulose, polyvinylpyrrolidone, hydroxypropylmethyl cellulose, microcrystalline cellulose in combination with lactose, microcrystalline cellulose in combination with sodium carboxymethyl cellulose, or a mixture of any of said pharmaceutical excipients.

10. A pharmaceutical composition as defined in claim 9 wherein said pharmaceutical excipient comprises microcrystalline cellulose.

11. A pharmaceutical composition as defined in claim 3 wherein said pharmaceutical excipient comprises microcrystalline cellulose, polyvinylpyrrolidone, hydroxypropylmethyl cellulose, microcrystalline cellulose in combination with lactose, microcrystalline cellulose in combination with sodium carboxymethylcellulose, or a mixture of any of the foregoing.

12. A pharmaceutical composition as defined in claim 11 wherein said pharmaceutical excipient comprises microcrystalline cellulose.

13. A pharmaceutical composition as defined in claim 1 wherein said 7- or 9-(lower)alkyl-amino-6-deoxy-6-demethyl tetracycline compound comprises from about 10 to about 70 parts by weight and said excipient comprises from about 90 to about 30 parts by weight per 100 parts by weight of said 7- or 9-(lower)alkyl-amino-6-deoxy-6-demethyl tetracycline compound and said excipient.

14. A pharmaceutical composition as defined in claim 3 wherein wherein said tetracycline compound comprises from about 10 to about 70 parts by weight and said excipient comprises from about 90 to about 30 parts by weight per 100 parts by weight of said tetracycline compound and said excipient.

15. A pharmaceutical composition as defined in claim 3 wherein said polymer is selected from
(a) methylcellulose;
(b) ethylcellulose;
(c) hydroxyethyl cellulose;
(d) hydroxypropyl cellulose;
(e) hydroxypropyl methylcellulose;
(f) hydroxypropyl methylcellulose phthalate;
(g) cellulose acetate phthalate
(h) hydroxypropyl methylcellulose succinate
(i) a polymer or copolymer of (meth)acrylic acid or an ester thereof; or
(j) a mixture of any of (a)–(i) alone or in further combination with a plasticizer, a colorant or a pigment.

16. A pharmaceutical composition as defined in claim 3 which also includes an ultrathin top layer of the same or a different polymer over an intermediate polymer layer.

17. A pharmaceutical composition as defined in claim 16 wherein the intermediate layer and the top layer comprise hydroxypropyl methylcellulose.

18. A pharmaceutical composition as defined in claim 3 wherein said polymer comprises from about 2 to less than about 10 percent by weight of the total weight of said polymer-coated spherical granules.

19. A pharmaceutical composition as defined in claim 18 wherein said polymer comprises from about 2 to about 5 percent by weight of the weight of said polymer-control spherical granules.

20. A pharmaceutical composition as defined in claim 1 wherein the spherical granules have an average diameter in the range of from about 0.1 to about 2.5 millimeters.

21. A pharmaceutical composition as defined in claim 20 wherein the spherical granules have an average diameter of from about 0.8 to about 1.2 millimeters.

22. A controlled release pharmaceutical composition in oral dosage unit form comprising
A. A gelatin capsule filled solely with
B. beads having an average diameter of from about 0.1 to about 2.5 millimeters, each bead being similar in composition and comprising spherical granules which include on or in said granules an effective antibacterial amount of a 7- or 9-(lower)alkylamino-6-deoxy-6-demethyltetracycline or a non-toxic acid addition salt thereof blended with an effective amount of at least one pharmaceutically acceptable excipient, said granules being adapted to control the rate of release of said 7- or 9-(lower)alkyl-amino-6-deoxy-6-demethyl tetracycline compound in the human stomach and in the human intestine upon oral administration.

23. A control release pharmaceutical composition as defined in claim 22 wherein controlling the rate comprises retarding the rate of release of said 7- or 9-(lower-)alkyl-amino-6-deoxy-6-demethyl tetracycline compound in the human stomach and promoting rapid release of said 7- or 9-(lower)alkyl-amino-6-deoxy-6-demethyl tetracycline compound in the human intesting upon oral administration.

24. A controlling release pharmaceutical composition as defined in claim 22 wherein each of said spherical granules includes an ultrathin layer of a polymer substantially uniformly coating each of said spherical granules, said polymer being slowly erodable in the human stomach and rapidly erodable in the human small intestine upon oral administration.

25. A controlled release pharmaceutical composition as defined in claim 22 wherein said 7- or 9-(lower)alkylamino-6-deoxy-6-demethyl tetracycline compound is selected from
(a) 7-dimethylamino-6-deoxy-6-demethyl tetracyline;
(b) 7-methylamino-6-deoxy-6-dimethyltetracycline;
(c) 9-methylamino-6-deoxy-6-demethyltetracycline;
(d) 7-ethylamino-6-deoxy-6-demethyltetracycline;
(e) 7-isopropylamino-6-deoxy-6-demethyltetracycline;
(f) a non-toxic acid addition salt of (a)–(e), inclusive; or
(g) a mixture of any of (a)–(f).

26. A controlled release pharmaceutical composition as defined in claim 25 wherein said 7- or 9-(lower)alkylamino-6-deoxy-6-demethyl tetracycline compound is selected from 7-dimethylamino6-deoxy-6-demethyl tetracycline or an acid addition salt thereof.

27. A controlled release pharmaceutical composition as defined in claim 26 wherein said 7- or 9-(lower)alkylamino-6-deoxy-6-tetracycline compound comprises 7-dimethylamino-6-deoxy-6-demethyltetracycline hydrochloride.

28. A controlled release pharmaceutical composition as defined in claim 22 wherein said pharmaceutical excipient comprises microcrystalline cellulose, polyvinylpyrrolidone, hydroxypropylmethyl cellulose, microcrystalline cellulose in combination with lactose, microcrystalline cellulose in combination with sodium carboxymethyl-cellulose, or a mixture of any of said pharmaceutical excipients.

29. A controlled release pharmaceutical composition as defined in claim 28 wherein said pharmaceutical excipient comprises microcrystalline cellulose.

30. A controlled release pharmaceutical composition as defined in claim 24 wherein said pharmaceutical excipient comprises microcrystalline cellulose, polyvinyl pyrrolidone, hydroxypropylmethyl cellulose, microcrystalline cellulose in combination with lactose, microcrystalline cellulose in combination with sodium carboxymethyl-cellulose, or a mixture of any of said pharmaceutical excipients.

31. A controlled release pharmaceutical composition as defined in claim 30 wherein said pharmaceutical excipient comprises microcrystalline cellulose.

32. A controlled release pharmaceutical composition as defined in claim 22 wherein in beads B said 7- or 9-(lower)alkyl-amino-6-deoxy-6-demethyl tetracycline compound comprises from about 10 to about 70 parts by weight and said excipient comprises from about 90 to about 30 parts by weight per 100 parts by weight of said 7- or 9-(lower)alkyl-amino-6-deoxy-6-demethyl tetracycline compound and said excipient.

33. A controlled release composition as defined in claim 24 wherein said beads B said 7- or 9-(lower)alkyl-amino-6-deoxy-6-demethyl tetracycline compound comprises from about 10 to about 70 parts by weight and said excipient comprises from about 90 to about 30 parts by weight per 100 parts by weight of said tetracycline compound and said excipient.

34. A controlled release pharmaceutical composition as defined in claim 22 wherein wherein said polymer is selected from
(a) methylcellulose;
(b) ethylcellulose;

(c) hydroxyethyl cellulose;
(d) hydroxypropyl cellulose;
(e) hydroxypropyl methylcellulose;
(f) hydroxypropyl methylcellulose phthalate;
(g) cellulose acetate phthalte
(h) hydroxypropyl methylcellulose succinate
(i) a polymer or copolymer of (meth)acrylic acid or an ester thereof; or
(j) a mixture of any of (a)–(i), or in further combination with a plasticizer, a colorant or a pigment.

35. A controlled release pharmaceutical composition as defined in claim 24 wherein beads B also include an ultrathin top layer of the same or a different polymer over intermediate layer.

36. A controlled release pharmaceutical composition as defined in claim 35 wherein the intermediate layer and the top layer comprise hydroxypropyl methylcellulose.

37. A controlled release pharmaceutical composition as defined in claim 24 wherein said polymer comprises from about 2 to less than about 10 percent by weight of the total weight of said polymer coated spheres.

38. A controlled release pharmaceutical composition as defined in claim 37 wherein said polymer comprises from about 2 to about 5 percent by weight of said polymer coated spheres.

39. A controlled release pharmaceutical composition as defined in claim 22 wherein said beads have an average diameter of from about 0.1 to about 2.5 millimeters.

40. A controlled release pharmaceutical composition as defined in claim 22 wherein each capsule contains from about 25 to about 200 mg of 7- or 9-(lower)alkylamino-6-deoxy-6-demethyl tetracycline compound.

41. A controlled release pharmaceutical composition as defined in claim 24 wherein each capsule contains from about 25 to about 200 of 7- or 9-(lower)alkylamino-6-deoxy-6-demethyl tetracycline compound.

42. A controlled release pharmaceutical composition as defined in claim 1 in oral dosage unit form comprising a tablet.

* * * * *

UNITED STATES PATENT AND TRADEMARK OFFICE
CERTIFICATE OF CORRECTION

PATENT NO. : 4,837,030

DATED : June 6, 1989

INVENTOR(S) : Joseph J. Valorose, Jr. et al.

It is certified that error appears in the above-identified patent and that said Letters Patent is hereby corrected as shown below:

Claim 1, line 1, delete "spheri-".

Claim 1, line 2, delete "cal".

Claim 1, line 2, after "comprising" insert --spherical--.

Claim 1, line 5, delete "said" and insert --salt--.

Claim 1, line 10, delete "intesting" and insert --intestine--.

Claim 5, line 7, delete "concention" and insert --concentration--.

Claim 14, line 2, delete "wherein" (second occurance).

Claim 19, line 4, delete "control" and insert --coated--.

Claim 24, line 1, delete "controlling" and insert --controlled--.

Claim 25, line 6, delete "dimethyltetracycline" and insert --demethyltetracycline--.

Claim 26, line 4, delete "7-dimethylamino6-deoxy-6-demethyl" and insert --7-dimethylamino-6-deoxy-6-demethyl--.

Claim 33, line 2, delete "said" (first occurance) and insert --in--.

UNITED STATES PATENT AND TRADEMARK OFFICE
CERTIFICATE OF CORRECTION

PATENT NO. : 4,837,030

DATED : June 6, 1989

INVENTOR(S) : Joseph J. Valorose, Jr. et al.

It is certified that error appears in the above-identified patent and that said Letters Patent is hereby corrected as shown below:

Claim 34, line 10, delete "phthalte" and insert --phthalate--.

Signed and Sealed this

Twenty-sixth Day of June, 1990

Attest:

HARRY F. MANBECK, JR.

*Attesting Officer*         *Commissioner of Patents and Trademarks*